(12) United States Patent
Halleck et al.

(10) Patent No.: US 6,356,203 B1
(45) Date of Patent: Mar. 12, 2002

(54) APPARATUS AND METHOD FOR DETECTING A ROTATIONAL MOVEMENT OF A BODY

(75) Inventors: Michael D. Halleck, Northglenn; Michael E. Halleck, Longmont, both of CO (US)

(73) Assignee: iLife Systems, Inc., Dallas, TX (US)

( * ) Notice: Subject to any disclaimer, the term of this patent is extended or adjusted under 35 U.S.C. 154(b) by 0 days.

(21) Appl. No.: 09/717,425

(22) Filed: Nov. 20, 2000

Related U.S. Application Data

(63) Continuation-in-part of application No. 09/542,197, filed on Apr. 4, 2000.

(51) Int. Cl.[7] ............................................. G08B 21/00
(52) U.S. Cl. .................. 340/689; 340/506; 340/517; 340/473.1; 340/686.1; 200/61.45 R; 200/61.52; 600/534
(58) Field of Search ........................... 340/689, 506, 340/517, 521, 527, 573.1, 686.1; 200/61.45 R, 61.52; 600/534, 536

(56) References Cited

U.S. PATENT DOCUMENTS

| | | | | |
|---|---|---|---|---|
| 4,617,525 A | * | 10/1986 | Lloyd ....................... | 340/573.1 |
| 4,972,177 A | * | 11/1990 | Nolan ....................... | 340/573.1 |
| 5,038,137 A | * | 8/1991 | Lloyd ....................... | 340/573.1 |
| 5,146,206 A | * | 9/1992 | Callaway .................. | 340/573.1 |
| 5,209,343 A | * | 5/1993 | Romano et al. .......... | 200/61.52 |
| 5,241,300 A | * | 8/1993 | Buschmann .............. | 340/573.1 |
| 5,554,975 A | * | 9/1996 | Hall et al. ................. | 340/573.1 |
| 5,615,688 A | * | 4/1997 | O'Dwyer ................... | 128/716 |
| 5,928,157 A | * | 7/1999 | O'Dwyer ................... | 600/534 |
| 6,095,991 A | * | 8/2000 | Krausmann et al. ..... | 600/595 |

* cited by examiner

*Primary Examiner*—Daniel J. Wu
*Assistant Examiner*—Toan Pham

(57) ABSTRACT

The present invention comprises an apparatus and method for detecting a rotational movement of a body. An advantageous embodiment of the invention is capable of detecting a rotational movement of the body of a child. The invention can provide a care giver information concerning the position of the body of a child in the care giver's care. The invention is especially useful in warning when a child moves from a position of lying on its back to a position of lying on its stomach. The invention comprises at least two tilt switches capable of detecting when the apparatus of the invention has been rotated by a preselected inclination angle of approximately one hundred eighty degrees. The invention also comprises a controller that is capable of receiving a signal from the tilt switches and generating an alarm signal. The apparatus also comprises an alarm signaling device that is capable of sending the alarm signal to alert a care giver that a child has rolled over onto his or her stomach. The alarm signaling device may be an audio speaker or may be a radio frequency transmitter capable of sending a radio signal to a base station radio receiver. The apparatus is also capable of initiating the operation of physiological condition monitors in response to an alarm signal. The apparatus is also capable of detecting a rotational movement of an inorganic body such as a shipping crate that contains a product that must be stored and shipped in an upright position.

9 Claims, 9 Drawing Sheets

APPARATUS AND METHOD FOR DETECTING A ROTATIONAL MOVEMENT OF A BODY

RELATED APPLICATIONS

This patent application is a continuation in part of co-pending U.S. patent application Ser. No. 09/542,197 filed Apr. 4, 2000 by Halleck et al. entitled "Apparatus and Method for Detecting An Inclination of A Body." The present invention is related to that disclosed in U.S. patent application Ser. No. 09/536,093 filed Mar. 24, 2000, entitled "Physiological Condition Monitors Utilizing Very Low Frequency Acoustic Signals." Both of the related patent applications are commonly assigned to the assignee of the present invention. The disclosures of both of the related patent applications are hereby incorporated by reference in the present application as if fully set forth herein.

TECHNICAL FIELD OF THE INVENTION

The present invention is directed to an apparatus and method for detecting a rotational movement of a body. An advantageous embodiment of the invention detects a rotational movement of the body of a child. The invention notifies a care giver that a child has moved from a position of lying on the back to a potentially unsafe position of lying on the stomach.

BACKGROUND OF THE INVENTION

In the United States an estimated three thousand infants a year suddenly die from unexplained causes. Apparently healthy children can suddenly die without any obvious cause of death. This phenomenon is known as Sudden Infant Death Syndrome. In the United States Sudden Infant Death Syndrome is the leading cause of death of children between the age of one month and one year. It is second only to congenital abnormalities as the leading overall cause of death for all children less than one year of age.

A potentially unsafe sleeping position for children is that of lying on the stomach. A child should lie on his or her back in order to reduce the risk of Sudden Infant Death Syndrome. There is therefore a need for an apparatus and method for detecting a rotational motion of a child to determine when a child has moved from a position of lying on the back to a position of lying on the stomach.

There is also a need to have an apparatus and method for immediately alerting a care giver that a child has moved from a position of lying on the back to a potentially unsafe position of lying on the stomach.

There is also a need for an apparatus and method for alerting a remotely located care giver that a child moved from a position of lying on the back to a potentially unsafe position of lying on the stomach.

If a child begins to experience difficulty in breathing, or begins to experience a high rate of heartbeat, or begins to experience a low rate of heartbeat, whoever is caring for the child (usually one of the child's parents) may have only a few seconds to respond to the child's distress. Therefore, it is very desirable to be able to provide a child's care giver with immediate notification that the child is experiencing cardiac or respiratory difficulty. This may be achieved by using a physiological condition monitor that is capable of continuously monitoring the physiological conditions of the child.

The present invention for detecting a rotational motion of the body of a child may be used in conjunction with physiological condition monitors. In particular, the present invention may be used in conjunction with the type of physiological condition monitors set forth and described in applicant's related U.S. patent application Ser. No. 09/536,093 filed Mar. 24, 2000, entitled "Physiological Condition Monitors Utilizing Very Low Frequency Acoustic Signals."

Physiological condition monitors are capable of obtaining and recording signals indicative of a child's physiological processes. The most commonly monitored physiological processes are respiration and cardiac activity. Physiological condition monitors that monitor respiration and cardiac activity usually comprise one or more sensors coupled to the body of the child whose physiological conditions are to be measured. The sensors are capable of sensing changes in pressure (or changes in other types of physical parameters) that are caused by the child's breathing and cardiac activity. Physiological condition monitors measure and record waveform signals received from the sensors. Electrocardiogram (ECG) waveform signals may be used to measure a child's cardiac activity. Respiration waveform signals are used to measure a child's breathing rate and other types of information concerning respiration.

Low heart rate is referred to as bradycardia. Cessation of respiration is referred to as apnea. When a child exhibits apnea or bradycardia a life threatening condition very likely exists. Physiological condition monitors that are capable of continuously monitoring a child's respiration and cardiac activity are extremely useful for quickly detecting apnea or bradycardia. Such physiological condition monitors are also useful for quickly detecting other abnormal conditions such as a high heart rate (known as tachycardia) or a very slow breathing rate or a very high breathing rate.

Children who are susceptible to Sudden Infant Death Syndrome are known to exhibit apnea and bradycardia. Physiological condition monitors that are capable of continually monitoring respiration and cardiac activity are particularly useful in the early detection of apnea or bradycardia in children. Most physiological condition monitors are equipped with an alarm system to sound an alert when such conditions are detected.

A physiological condition monitor may be coupled directly to a child while the child is lying in a bed. In such an arrangement the waveform signals from the sensors coupled to the child's body may be sent through wires directly to a detector circuit (and other circuitry) located in a console by the child's bed. The wires attached to the child restrict the child's movements.

In other cases it is more practical to provide a physiological condition monitor located in a belt or harness that is to be worn by the child. In this type of monitor the waveform signal information from the sensors is transmitted via a radio frequency transmitter to a radio frequency receiver in a base station unit that is located away from the site of the physiological condition monitor. The base station unit contains circuitry for analyzing and recording the waveform signal information. The base station unit contains circuitry for detecting abnormal conditions in the child's breathing (such as apnea) or abnormal conditions in the child's cardiac activity (such as bradycardia or tachycardia). Because of the freedom of movement that this type of monitor provides, it is the preferred type of monitor for monitoring the physiological conditions of children.

If the data that is acquired by the physiological condition monitor is not transmitted to the base station and recorded there, then the data must be recorded in a memory data storage device located within the physiological condition monitor. To preserve the freedom of movement that is provided by a belt or harness monitor, the memory data storage device within the physiological condition monitor must be battery powered.

Electrocardiogram (ECG) waveform signals may be used to obtain information concerning a child's cardiac activity. To obtain ECG waveforms an ECG sensor unit is coupled to the child. The ECG sensor unit is coupled to the child via electrodes capable of receiving cardiac activity signals directly from the child's body. In such an arrangement the electrodes must be attached directly to the child's skin in order to receive the signals. The ECG sensor unit receives the ECG electrical signals from the electrodes. The ECG signals received by the ECG sensor unit are then either recorded within the physiological condition monitor or transmitted to a base station unit.

The present invention for detecting a rotational motion of the body of a child may be used to initiate monitoring by physiological condition monitors. When a child is lying on his or her back, it may be unnecessary for the physiological condition monitors to be operating continuously. In an advantageous embodiment of the present invention, the operation of the physiological condition monitors is not initiated until the present invention detects a rotational motion of the child that places the child in the potentially unsafe position of lying on the stomach. When the present invention detects a rotational movement of the child that causes the child to roll onto his or her stomach, the present invention generates a signal that automatically initiates the operation of the physiological condition monitors. The present invention also sends a signal to the care giver that informs the care giver that the operation of the physiological condition monitors has been initiated.

SUMMARY OF THE INVENTION

The present invention is directed to an apparatus and method for detecting a rotational movement of a body. An advantageous embodiment of the invention detects a rotational movement of the body of a child. The invention notifies a care giver that a child has moved from a position of lying on the back to a potentially unsafe position of lying on the stomach.

The apparatus of the invention comprises at least a first tilt switch connected in series with a second tilt switch. A child in a bed can roll over to the left one hundred eighty degrees (180°) or to the right one hundred eighty degrees (180°). The spatial relationship of the tilt switches connected in series make the tilt switches capable of detecting when the body of the child has been rotated around a reference axis of rotation by one hundred eighty degrees (180°) in either direction.

When the body of the child rotates around the reference axis by one hundred eighty degrees (180°), the tilt switches in the apparatus of the present invention generate a signal that indicates that the child has rolled over onto his or her stomach. The tilt switches send the signal to a controller. The controller receives the signal from the tilt switches and causes a radio frequency transmitter to transmit an alarm signal to a base station that is monitored by a care giver. Alternatively, the controller transmits the alarm signal to a sound alarm that is capable of causing an audio speaker to make a loud audible sound.

In either case, the care giver is thereby immediately notified that the child has rolled over onto his or her stomach. The care giver is then able to respond and turn the child over so that the child is once again lying on his or her back.

It is a primary object of the present invention to provide an apparatus and method for detecting when the body of a child has been rotated around a reference axis of rotation by one hundred eighty degrees (180°) in either direction.

It is a further object of the present invention to provide an apparatus and method for detecting a rotational motion of a child in order to immediately notify a care giver that a child has moved from a position of lying on the back to a potentially unsafe position of lying on the stomach.

It is also an object of the present invention to provide an apparatus and method for notifying a remotely located care giver that a child moved from a position of lying on the back to a potentially unsafe position of lying on the stomach It is a further object of the present invention to provide an apparatus and method for initiating the operation of physiological condition monitors whenever the present invention detects a rotational movement of a child that causes the child to move from a position of lying on the back to a potentially unsafe position of lying on the stomach.

It is also an object of the present invention to provide an apparatus and method for sending coded messages to a care giver who simultaneously monitors the status of several children to provide the care giver with information concerning the status of the position of each of the children and concerning the operational status of the apparatus.

It is also an object of the present invention to provide an apparatus and method for sending coded messages to a care giver who simultaneously monitors the status of the position of each of several children to provide the care giver with information concerning the operational status of the apparatus.

It is also an object of the present invention to provide an apparatus and method for detecting a rotational movement of an inorganic body such as a shipping crate that contains a product that must be stored and shipped in an upright position.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description, it may be advantageous to set forth definitions of certain words and phrases used throughout this patent document: the terms "include" and "comprise" and derivatives thereof mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware, or software, or some combination of at least two of the same. In particular, a controller may be a data processor capable of executing an application program stored in a memory, such as a random access memory (RAM), coupled to the data processor. It should be noted that the functionality associated with any particular controller may be centralized or distributed, whether locally or remotely. Definitions for certain words and phrases are provided throughout this patent document. Those of ordinary skill in the art should understand that in many, if not most, instances, such definitions apply to prior, as well as future uses of such defined words and phrases.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which.

DETAILED DESCRIPTION

FIGS. 1 through 11, discussed below, and the various embodiments used to describe the principles of the present invention in this patent document are by way of illustration only and should not be construed in any way to limit the scope of the invention. Those skilled in the art will understand that the principles of the present invention may be implemented in a suitably modified apparatus for detecting a rotation of a body.

The term "body" is defined broadly, meaning any organic or inorganic object whose movement or position may be evaluated relative to its environment. For purposes of illustration the principles of operation of the present invention will be described with respect to an apparatus and method for detecting a rotational movement of the body of a child. The present invention, however, is capable of detecting rotational movement of both organic bodies and inorganic bodies.

Figure 1:
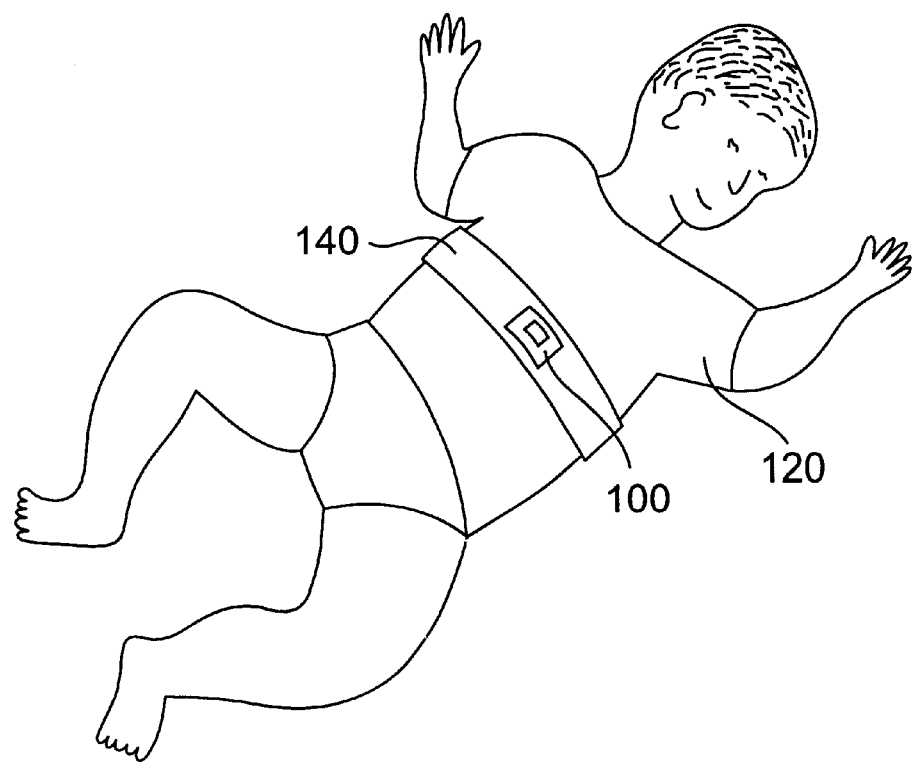
FIG. 1 is a drawing showing a child lying on his back who is wearing a belt with the apparatus of the present invention mounted on the belt.

FIG. 1 is a drawing illustrating how apparatus 100 of the present invention may be worn by a child 120. Although child 120 may be either a male child or a female child, for purposes of illustration child 120 will be assumed to be a male child. Child 120 in FIG. 1 is wearing apparatus 100 of the present invention on a belt 140 that is fastened around the child's torso. Apparatus 100 may be worn under or over the clothes of child 120. Apparatus 100 may also be placed in a pocket (not shown) of the clothes of child 120 as long as apparatus 100 is appropriately aligned and positioned within the pocket. When child 120 is lying on his back as shown, apparatus 100 is aligned with the level of bed (not shown). As will be seen from the discussion below, apparatus 100 will detect the rotational motion of the child's torso when the child 120 rolls over onto his stomach.

Figure 2:
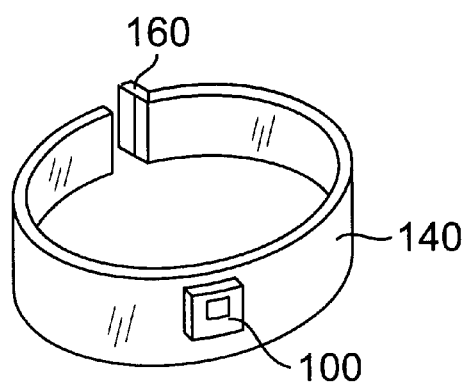
FIG. 2 is a perspective view of the belt and apparatus shown in FIG. 1 showing the placement of the apparatus of the present invention on the belt.

FIG. 2 is a perspective view of apparatus 100 and belt 140 showing the placement of apparatus 100 on 140 belt. Belt 140 also has a clasp 160 for fastening (and unfastening) belt 140 around the torso of child 120.

Figure 3:
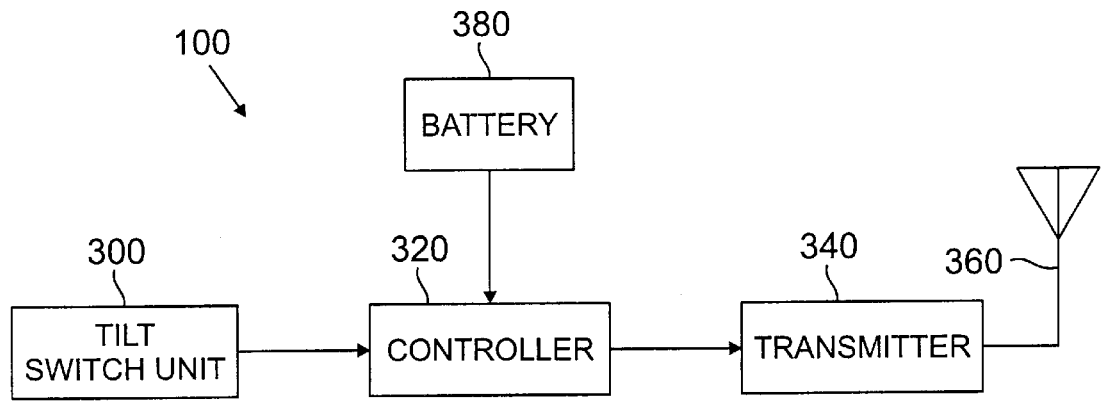
FIG. 3 is a block diagram of the present invention showing the interconnection of a tilt switch unit and a controller and a transmitter and an antenna.

FIG. 3 is a block diagram of the apparatus 100 of the present invention showing a tilt switch unit 300 coupled to a controller 320. Radio frequency transmitter 340 is coupled to controller 320. Antenna 360 is coupled to transmitter 340. Battery 380 is coupled to controller 320 and supplies electrical power for the operation of controller 320. Although battery 380 is shown coupled only to controller 320 in FIG. 3 (and in FIG. 4 and in FIG. 8), battery 380 is connected to and provides electrical power to all components of apparatus 100 through other electrical connections (not shown).

Tilt switch unit 300 detects when apparatus 100 has been rotated by one hundred eighty degrees (180°) to the right or to the left with respect to a vertical reference axis of rotation through the body of child 120. The vertical reference axis of rotation is the head-to-foot axis of the body of child 120. When child 120 rolls over from his back to his stomach (either to the right or to the left), then tilt switch unit 300 of apparatus 100 generates an signal that indicates that tilt switch unit 300 is in a closed position. The signal may take the form of an interrupt signal that tilt switch unit 300 sends to controller 320.

When controller 320 receives a signal from tilt switch unit 300, controller 320 immediately begins to time the duration of the signal. If the signal from tilt switch unit 300 ends within a preselected time limit, then controller 320 ignores the signal. Although any duration for the preselected time limit may be selected, for purposes of illustration the preselected time limit will be selected to be two (2) seconds. If the duration of the signal exceeds the two (2) second time limit, controller 320 generates an alarm signal for radio frequency transmitter 340. Therefore, the criterion for generating an alarm signal in this example is that tilt switch unit 300 remains in a closed position for more than two (2) seconds.

When the alarm signal is received from controller 320, then radio frequency transmitter 340 transmits an alarm signal to a base station radio receiver (not shown in FIG. 3) that is monitored by a care giver. The care giver is thereby immediately alerted that the child 120 (to whom apparatus 100 is attached) has rolled over onto his stomach. The care giver is then able to respond and turn the child 120 back over on his back.

After controller 320 has generated and sent an alarm signal to radio frequency transmitter 340, controller 320 turns off the alarm signal to transmitter 340 after a preselected time limit has elapsed. Although any duration for the preselected time limit may be selected, for purposes of illustration the preselected time limit will be selected to be two hundred fifty microseconds (250 μs). A microsecond is equal to one millionth of a second. Radio frequency transmitter 340 responds to the alarm signal from controller 320 and generates and transmits an alarm signal of longer duration through antenna 360. The duration of the longer alarm signal of transmitter 340 may be selected to have sufficient length to provide adequate notice to the care giver.

After the preselected time limit of two hundred fifty microseconds (250 μs) has elapsed controller 320 turns off the alarm signal to transmitter 340. Controller 320 is then capable of generating another alarm signal whenever the tilt switches of tilt switch unit 300 are closed.

In an alternate embodiment of the invention, controller 320 may enable the alarm signal until controller 320 receives an alarm disable signal. The alarm disable signal may be manually entered in controller 320. Alternatively, the alarm disable signal may be a radio signal transmitted to a radio receiver (not shown) coupled to controller 320.

Controller 320 may also generate and send a unique identification code that uniquely identifies controller 320 as the source of the alarm signal. The identification code may also be transmitted with the alarm signal by transmitter 340. The identification code is useful in institutional settings where many units of apparatus 100 (each with its own separate controller 320) are used to monitor many children simultaneously. The institutional care giver at the base station who is monitoring many different units of apparatus 100 (each with its own identification code) can use a unique identification code to immediately determine which child 120 caused an alarm signal to sound.

Controller 320 may also determine when battery 380 is in a low voltage condition. If the voltage level of battery 380 is allowed to become too low, apparatus 100 will not operate. In an advantageous embodiment of the present invention controller 320 periodically determines the operating status of battery 380. For example, controller 320 can determine the operating status of battery 380 at least once every twenty four hours. When controller 320 detects a low voltage condition in battery 380, controller 320 generates and sends an alarm signal that is identical to the alarm signal that controller 320 generates and sends when tilt switch unit 300 is activated.

In this case, however, controller 320 also generates and sends a low battery code to identify that the alarm signal relates to a low battery condition. Controller 320 may also add a unique identification code that identifies a particular controller 320 as the source of the low battery alarm signal. The institutional care giver who is monitoring the base station may use the identification code to immediately determine which apparatus 100 has a battery 380 with an unacceptably low level of voltage.

Figure 4:
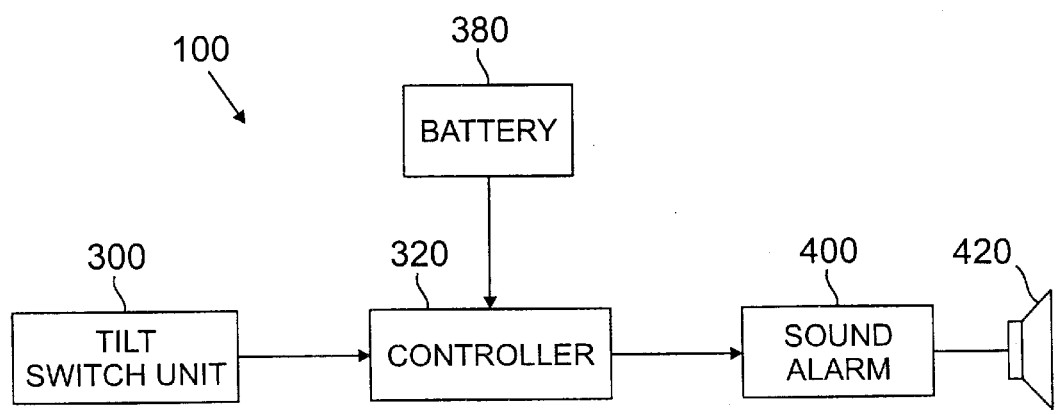
FIG. 4 is a block diagram of the present invention showing the interconnection of a tilt switch unit and a controller and a sound alarm and an audio speaker.

FIG. 4 shows an alternate embodiment of apparatus 100 in which radio frequency transmitter 340 and antenna 360 have been replaced with sound alarm unit 400 and speaker 420. In this embodiment of the invention, when controller 320 receives an inclination signal from tilt switch unit 300 indicating that the child 120 has rolled over onto his stomach, controller 320 sends an alarm signal to sound alarm unit 400. Sound alarm unit 400 then causes audio speaker 420 to make a loud audible sound. A care giver within earshot of audio speaker 420 is thereby immediately alerted that the child 120 has rolled over onto his stomach.

The care giver is then able to respond and turn the child 120 back over onto his back.

In an alternate embodiment of the present invention (not shown) apparatus 100 comprises (1) a first circuit branch coupled to controller 320 where the first circuit branch comprises radio frequency transmitter 340 and antenna 360, and (2) a second circuit branch coupled to controller 320 where the second circuit branch comprises sound alarm unit 400 and speaker 420. This embodiment of the present invention combines the embodiment shown in FIG. 3 and the embodiment shown in FIG. 4.

Figure 5:
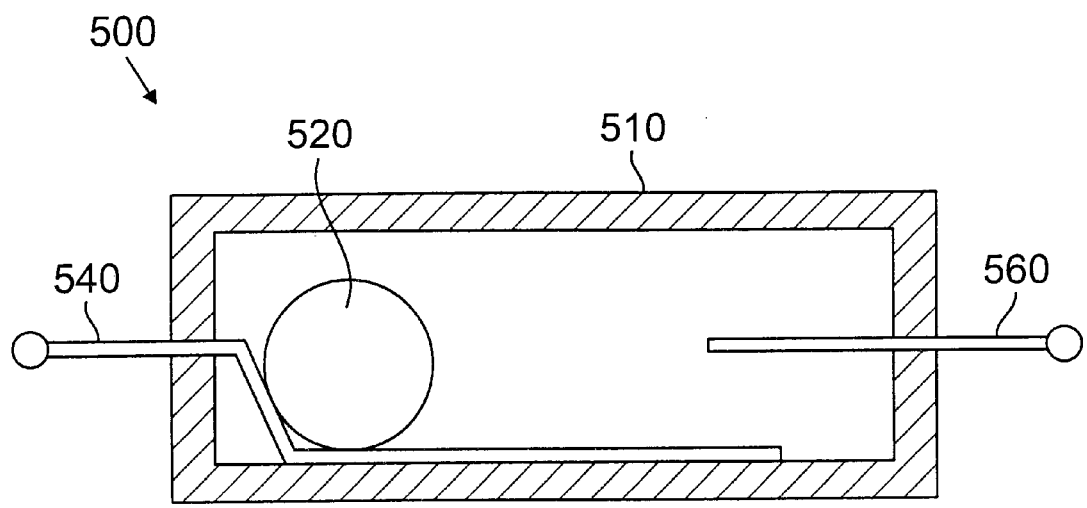
FIG. 5 is a schematic drawing of one embodiment of a tilt switch capable of being used in the tilt switch unit of the present invention.

FIG. 5 is a schematic drawing of one embodiment of a tilt switch 500 that is capable of being used in the tilt switch unit 300 of the present invention. Tilt switch 500 comprises an enclosure 510 that completely encloses a metal ball 520 and two electrodes, 540 and 560. Electrode 540 is in the form of an elongated metal plate on which metal ball 520 may roll. The enclosure 510 of tilt switch 500 is preferably filled with an inert non-conductive viscous liquid. The viscosity of the liquid prevents metal ball 520 from accidently rolling into contact with electrodes, 540 and 560. That is, metal ball 520 will not roll into contact with electrodes, 540 and 560, until a rotational movement of child 120 causes apparatus 100 to rotate by an amount sufficient to roll metal ball 520 into contact with the electrodes, 540 and 560. The non-conductivity of the liquid prevents electrical contact between electrodes, 540 and 560, until they are both touched by metal ball 520.

When enclosure 510 is tilted toward the left in FIG. 5, metal ball 520 rests on a portion of electrode 540 and makes no electrical contact with electrode 560. When enclosure 500 is tilted toward the right in FIG. 5, metal ball 520 rolls along electrode 540 (though the inert non-conducting viscous liquid) and comes into contact with electrode 560. This causes electrical contact between electrode 540 and electrode 560 though electrically conducting metal ball 520. This causes an electrical path to form through electrode 540, metal ball 520 and electrode 560, thereby closing tilt switch 500.

Figure 6:
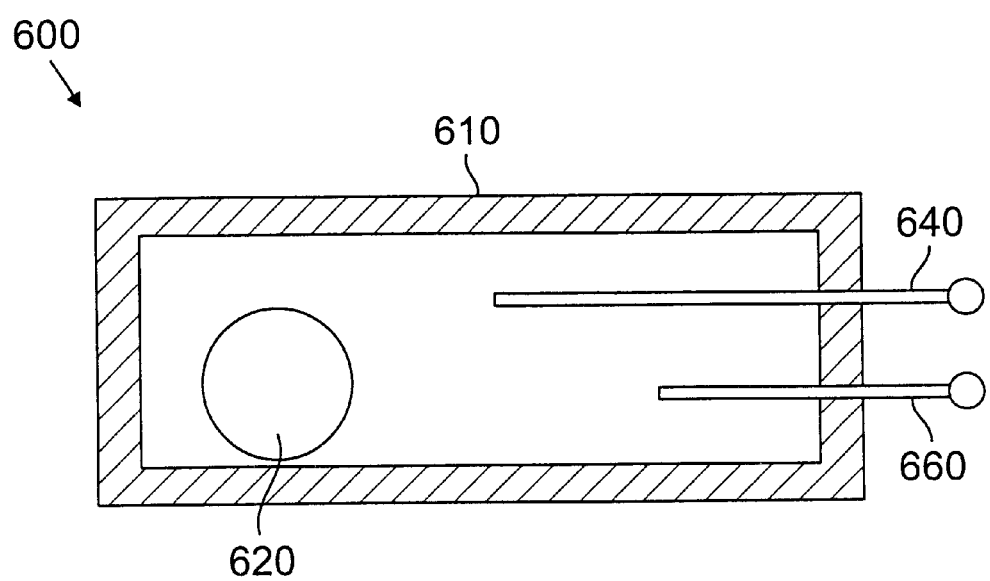
FIG. 6 is a schematic drawing of an alternate embodiment of a tilt switch capable of being used in the tilt switch unit of the present invention.

FIG. 6 is a schematic drawing of an alternate embodiment of a tilt switch 600 that is capable of being used in the tilt switch unit 300 of the present invention. Tilt switch 600 comprises an enclosure 610 that completely encloses a ball 620 of liquid mercury and two electrodes, 640 and 660. Mercury is a liquid metal at room temperature and forms into a ball due to surface tension. In an advantageous embodiment of the present invention, enclosure 610 is made of glass. It is clear, however, that other electrically non-conducting materials can be used to construct enclosure 610.

Electrode 640 and electrode 660 are aligned in parallel at one end of enclosure 600. Electrode 640 is longer than electrode 660 as shown in FIG. 6. When enclosure 610 is tilted toward the left in FIG. 6, liquid mercury ball 620 rests on the end of enclosure 600 opposite from the end of enclosure 610 that contains electrodes, 640 and 660, and there is no electrical contact between electrodes, 640 and 660.

When enclosure 610 is tilted toward the right in FIG. 5, liquid mercury ball 620 slides into contact with electrode 640. When the angle of tilt toward the right becomes sufficiently great, the weight of the mercury in liquid mercury ball 620 exceeds the surface tension of liquid mercury ball 620. Then the mercury in liquid mercury ball 620 ceases to take the form of a ball and flows into contact with electrodes, 640 and 660. The existence of a continuous mercury path between electrode 640 and electrode 660 causes electrical contact between electrode 640 and electrode 660 though the electrically conducting liquid mercury. Tilt switch 600 is then in a closed condition.

Figure 7A:
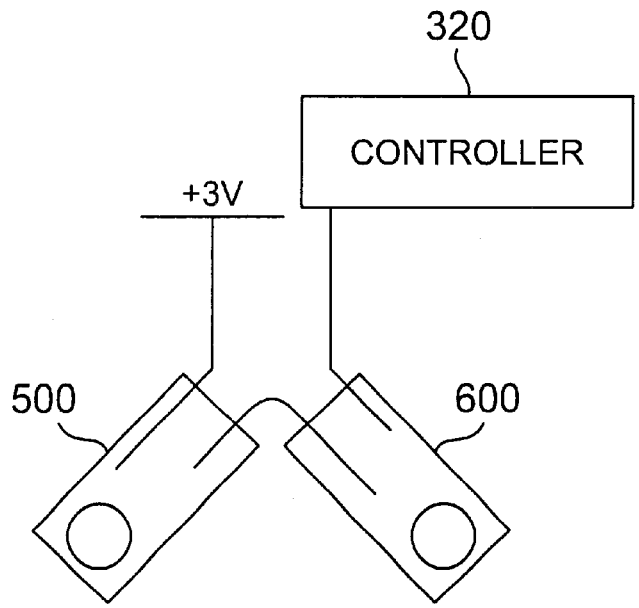
FIGS. 7a–7d are schematic drawings of the tilt switch unit of the present invention showing a first tilt switch in series with a second tilt switch in four different orientations.

FIG. 7a is a schematic drawing of tilt switch unit 300 of an advantageous embodiment of the present invention showing a first tilt switch 500 in series with a second tilt switch 600. In the position of tilt switch unit 300 shown in FIG. 7a the child 120 is lying on his back. There is no alarm signal because the tilt switches 500 and 600 are not closed.

Figure 7B:
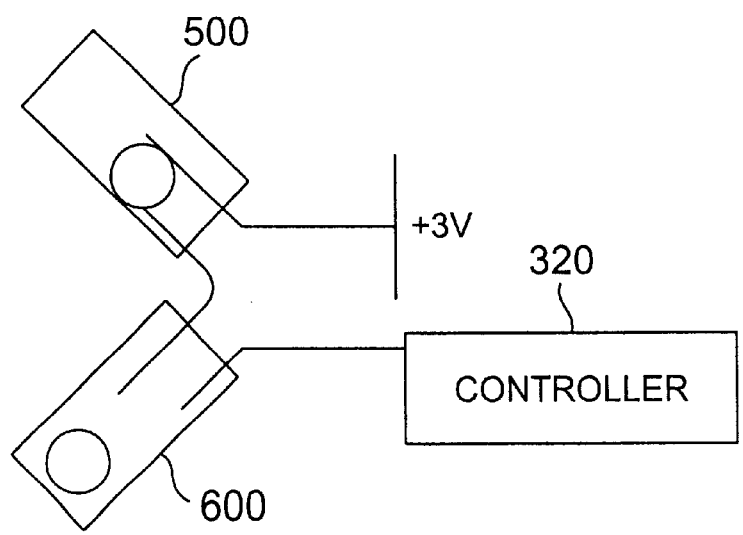
Figure 7C:
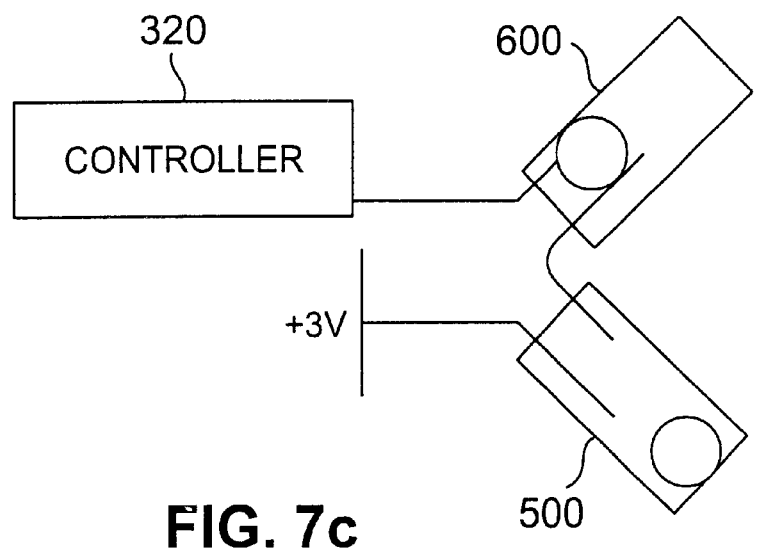

When the child 120 is lying on his right side the position of tilt switch unit 300 is shown in FIG. 7b. There is no alarm signal because only one of the switches is closed. Both tilt switch 500 and tilt switch 600 must be closed for the alarm to sound. Similarly, when the child 120 is lying on his left side the position of tilt switch unit 300 is shown in FIG. 7c. As before, there is no alarm signal because only one of the switches is closed and both tilt switch 500 and tilt switch 600 must be closed for the alarm to sound.

Figure 7D:
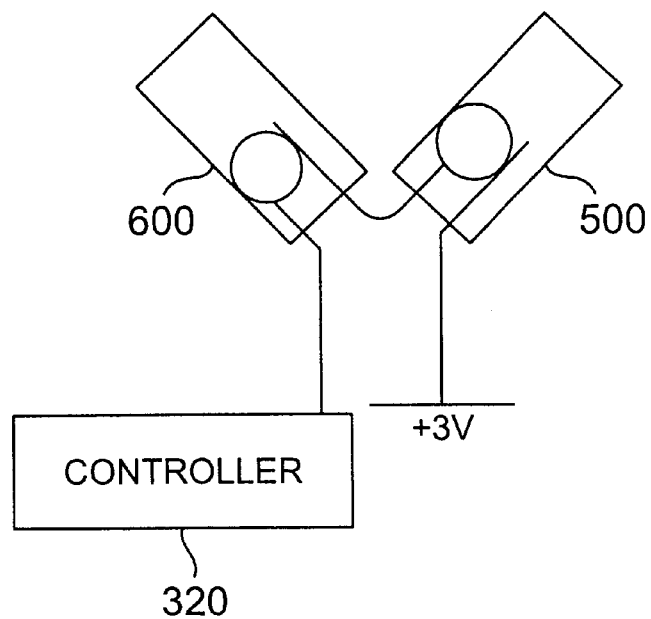

When the child 120 is in a prone position (i.e., lying on his stomach) the position of tilt switch unit 300 is shown in FIG. 7d. There is an alarm signal because both of the switches 500 and 600 are closed.

Figure 8:
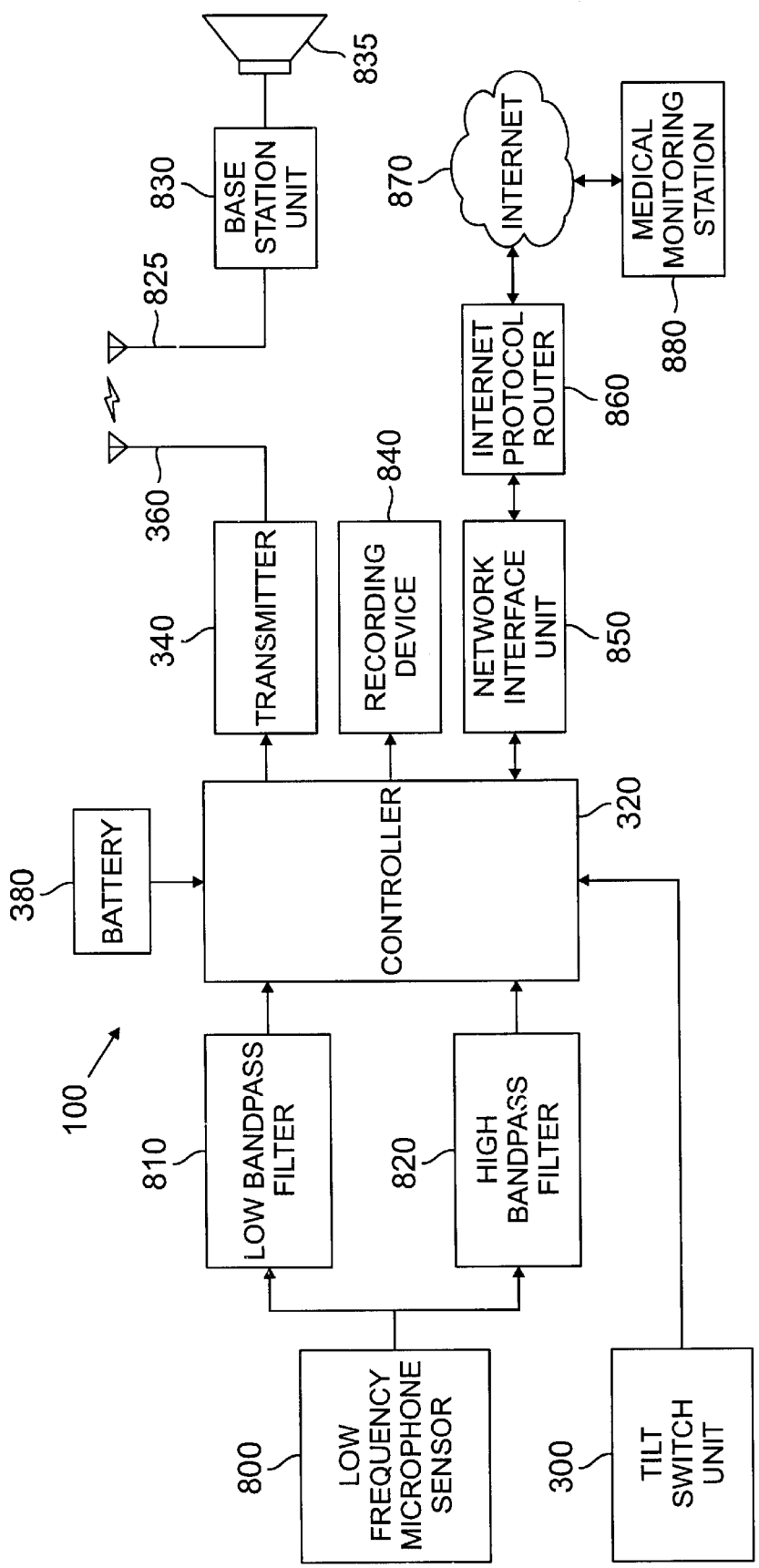
FIG. 8 is a block diagram of an advantageous embodiment of the present invention showing a tilt switch unit that is capable of initiating the operation of physiological condition monitors.

FIG. 8 is a block diagram illustrating the interconnection of tilt switch unit 300 and physiological condition monitors within apparatus 100. As will be more fully described, tilt switch unit 300 may be used to send a signal to controller 320 to initiate the operation of the physiological condition monitors.

A low frequency microphone sensor 800 in apparatus 100 receives low frequency signals from the body of child 120. The low frequency signals are created by the physiological conditions that are being monitored in child 120. Low frequency microphone sensor 800 detects and amplifies the signals as described in patent application Ser. No. 09/536,093 filed Mar. 24, 2000, entitled "Physiological Condition Monitors Utilizing Very Low Frequency Acoustic Signals." Although a low frequency microphone sensor 800 has been described, the present invention may be used with any type of sensor that is capable of obtaining electronic signals that represent one or more physiological conditions of child 120.

As shown in FIG. 8, the output of low frequency microphone sensor 800 is coupled to an input of low bandpass filter 810. Low bandpass filter 810 screens out all frequencies except those frequencies in the frequency bandwidth range from one tenth Hertz (0.1 Hz) to two Hertz (2.0 Hz). Low bandpass filter 810 may comprise conventional electronic filter circuits. Low bandpass filter 810 may also comprise electronic circuitry that utilizes computer software to achieve the bandpass filter function by digital signal processing. The output of low bandpass filter 810 is a digitally encoded very low frequency signal representative of the respiration of the child 120 being monitored.

The output of low frequency microphone sensor 800 is also coupled to an input of high bandpass filter 820. High bandpass filter 820 screens out all frequencies except those frequencies in the frequency bandwidth range from ten Hertz (10.0 Hz) to thirty Hertz (30.0 Hz). High bandpass filter 820 may comprise conventional electronic filter circuits. High bandpass filter 820 may also comprise electronic circuitry that utilizes computer software to achieve the bandpass filter function by digital signal processing. The output of high bandpass filter 820 is a digitally encoded very low frequency signal representative of the cardiac activity of the child 120 being monitored.

The output of low bandpass filter 810 and the output of high bandpass filter 820 are coupled to controller 320.

Controller 320 is capable of receiving digitally encoded signals from low bandpass filter 810 and from high bandpass filter 820. As previously described, battery 380 is coupled to controller 320 and is capable of supplying electrical power for the operation of controller 320 and other components of apparatus 100. Controller 320 is capable of detecting a signal from battery 380 that indicates that the voltage level of battery 380 is low.

In one embodiment of the present invention, controller 320 is coupled to radio frequency transmitter 340, which is itself coupled to antenna 360. Controller 320 is capable of selectively causing radio frequency transmitter 340 to transmit digitally encoded signals from low band pass filter 810 and digitally encoded signals from high band pass filter 820 to base station unit 830 via transmitter 340 and antenna 360. The digitally encoded signals are received by base station unit 830 via antenna 825. The received signals may then be displayed and analyzed at base station unit 830.

Controller 320 is capable of causing radio frequency transmitter 340 to transmit a signal to base station unit 830 that indicates that the voltage level of battery 380 is low. Controller 320 is also capable of causing radio frequency transmitter 340 to transmit a signal to base station unit 830 that indicates that controller 320 is not receiving signals from low bandpass filter 810 or from high bandpass filter 820. That is, controller 320 can transmit to base station unit 830 a signal indicating that one (or both) of the physiological conditions (breathing and heartbeat) is not being monitored.

Base station unit 830 is capable of sounding an alarm if an analysis of the received signals indicates an abnormal condition in the child 120 being monitored. Base station unit 830 comprises speaker 835 which may be activated to sound an alarm when base station unit 830 receives one or more signals indicating that (1) the child's breathing is irregular or has stopped, (2) the child's heartbeat is too fast, or is too slow, or has stopped, or (3) the child's breathing is not being monitored, or (4) the child's heartbeat is not being monitored, or (5) the battery voltage level is too low. Base station 830 is to be placed where a care giver who is monitoring base station 830 can hear the alarm whenever the alarm sounds.

In this manner, the child's care giver can immediately respond to the alarm to determine what condition exists. If the child is in physiological distress, the child's care giver can immediately attempt to relieve that distress. For example, if the child has ceased breathing, the care giver could immediately administer cardio-pulmonary resuscitation (CPR) to the child. If the alarm indicates a low battery or failure of monitoring function, remedial steps can be taken immediately.

One advantageous embodiment of the physiological condition monitors in apparatus 100 comprises low frequency microphone sensor 800, low bandpass filter 810, high bandpass filter 820, controller 320, battery 380, transmitter 340 and antenna 360. Apparatus 100 is capable of being coupled to a belt, harness or item of clothing that may be worn by the child being monitored. In this embodiment of apparatus 100 the movements of the child 120 being monitored are not restricted.

In an alternate advantageous embodiment of apparatus 100 controller 320 is coupled to recording device 840. Controller 320 sends digitally encoded signals from low band pass filter 810 and digitally encoded signals from high band pass filter 820 to recording device 840. Recording device 840 is preferably a non-volatile data storage device such as a magnetic tape recorder or a flash memory data storage card. A non-volatile data storage device is a device that retains the data stored in it when external power to the device is shut off.

In an additional advantageous embodiment of apparatus 100 controller 320 is coupled to network interface unit 850. Network interface unit 850 is capable of being coupled to a computer network such as a local area network (LAN), or a wide area network (WAN), or the Internet. The connection of network interface unit 850 to a computer network may be a wired connection or wireless connection.

In FIG. 8 network interface unit 850 is shown coupled to the Internet 870 via an Internet protocol router 860. Controller 320 sends digitally encoded signals from low band pass filter 810 and digitally encoded signals from high band pass filter 820 to network interface unit 850. Network interface unit 850 adapts the data to be transmitted via Internet protocol router 860 to the Internet 870. In this manner the data can be sent to medical monitoring station 880 at a remote location. Medical monitoring station 880 can be located in a hospital, a doctor's office, a clinic, a care giver facility, or any similar type of location.

In an alternate advantageous embodiment of apparatus 100 controller 320 is not coupled to transmitter 340 and to antenna 360. Instead controller 320 is coupled directly by wire to a wired base station unit (not shown) of the type described above. The wired base station unit is usually located in a console by the bed or chair of the child being monitored. As in the previously described case of base station unit 830, the wired base station unit is capable of displaying and analyzing digitally encoded signals from controller 320. The wired base station unit is capable of sounding an alarm if an analysis of the digitally encoded signals indicates an abnormal condition in the person being monitored. In this embodiment the wires coupling apparatus 100 to the wired base unit do restrict the movements of the child being monitored.

The tilt switch unit 300 of the present invention for detecting a rotational motion of the body of a child 120 may be used to initiate the process of monitoring the physiological conditions of the child 120. When the child 120 is lying on his back, it may be unnecessary for the physiological condition monitors to be operating continuously. In an advantageous embodiment of the present invention, the operation of the physiological condition monitors is not initiated until tilt switch unit 300 detects a rotational motion of the child 120 that places the child 120 in the potentially unsafe position of lying on his stomach. When tilt switch unit 300 detects a rotational movement of the child 120 that causes the child 120 to roll over onto his stomach, tilt switch unit 300 sends a signal to controller 320. When controller 320 receives the "rollover" signal from tilt switch unit 300, then controller 320 sends a signal to low frequency microphone sensor 800 via a control signal line (not shown) to initiate the operation of low frequency microphone sensor 800 to monitor the physiological conditions of the child 120. Controller 320 also sends a signal to the care giver that informs the care giver that the low frequency microphone sensor 800 has begun to monitor the physiological conditions of the child 120.

Figure 9:
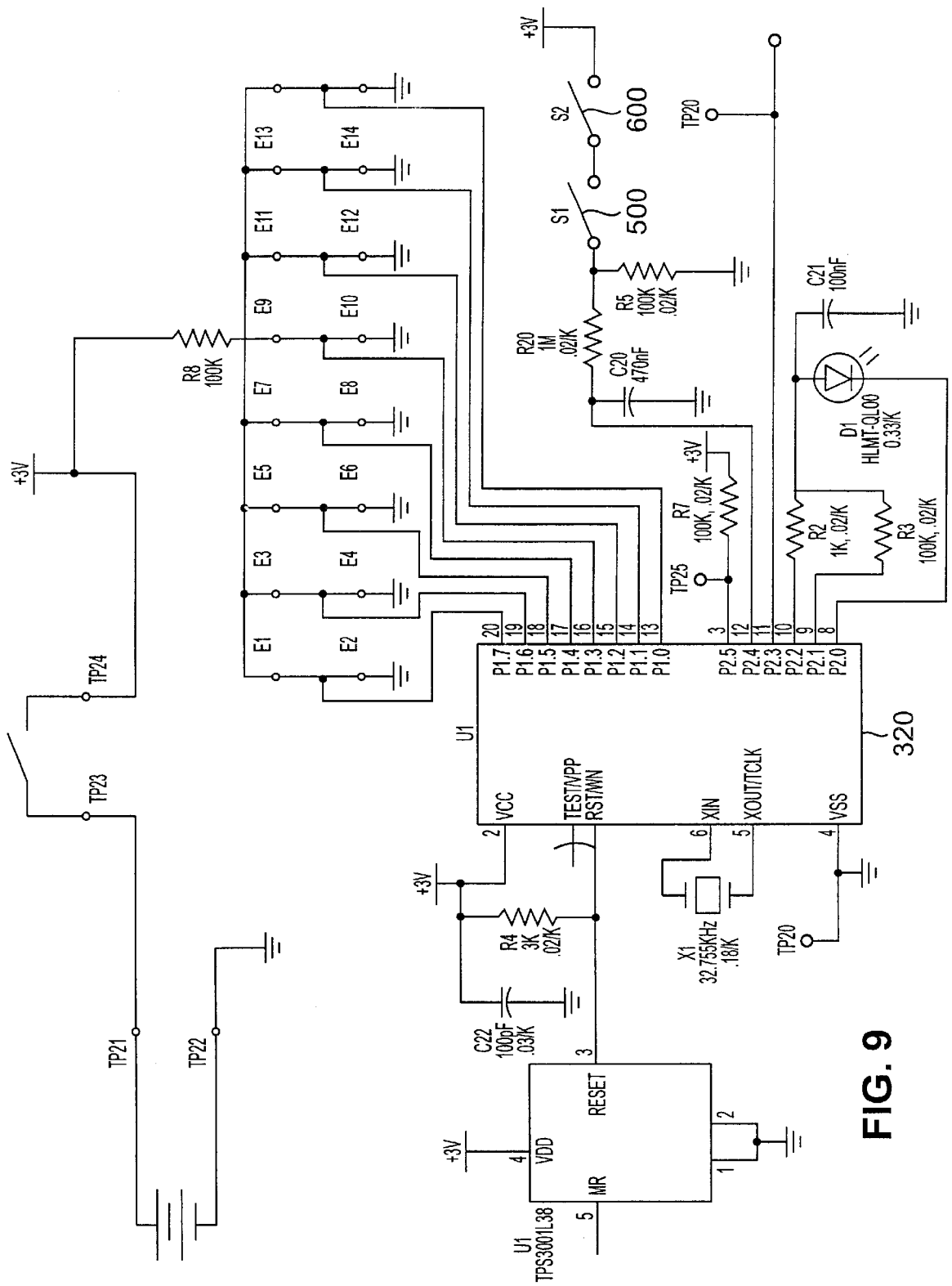
FIG. 9 is a detailed circuit diagram showing the interconnection of the two tilt switches and the controller of the present invention.

FIG. 9 is a detailed circuit diagram showing the interconnection of tilt switch 500 and tilt switch 600 in series and the interconnection of controller 320. One end of tilt switch 500 (referred to in FIG. 9 as "S1") is connected to input pin 12 (labeled "P2.4") of controller 320. The other end of tilt switch 500 is connected to one end of tilt switch 600 (referred to in FIG. 9 as "S2"). The other end of tilt switch 600 is connected to battery 380 (shown in FIG. 9 as a three volt (+3 V) power supply). When both tilt switch 500 and tilt switch 600 become closed due to the tilt of apparatus 100, the circuit branch containing tilt switches 500 and 600 generates an interrupt signal to controller 320. Controller 320 interprets the interrupt signal as an alarm inclination signal indicating that tilt switch unit 300 has the orientation shown in FIG. 7d indicating that the child 120 has rolled over from his back to his stomach.

Figure 10:
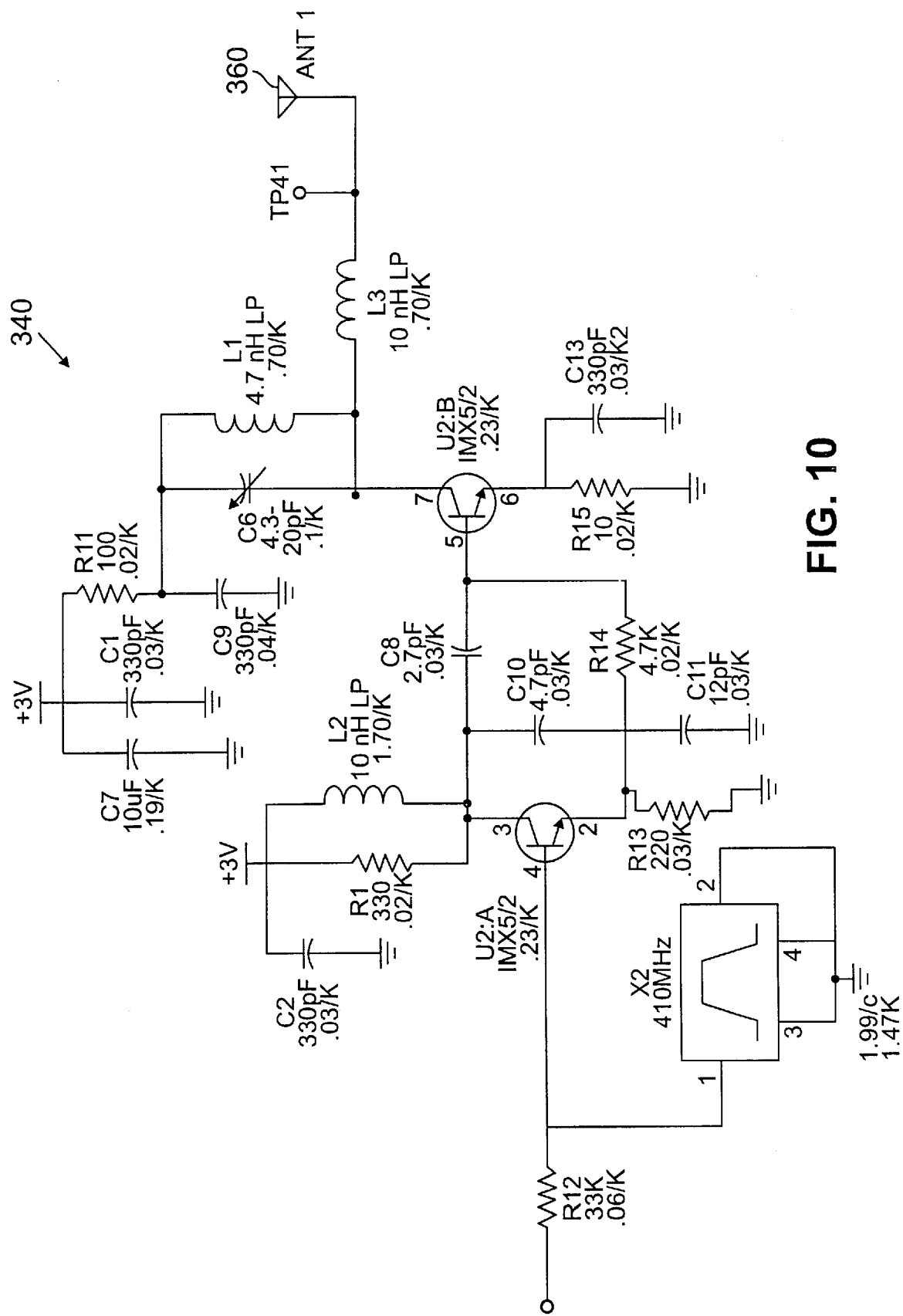
FIG. 10 is a detailed circuit diagram of a transmitter for use with the present invention.

FIG. 10 is a detailed circuit diagram of one embodiment of 340 transmitter and antenna 360 that can be used with apparatus 100 of the present invention. The transmitter 340 is of a conventional type and is designed to transmit a radio signal at a radio frequency of four hundred eighteen megahertz (418 MHz).

Figure 11:
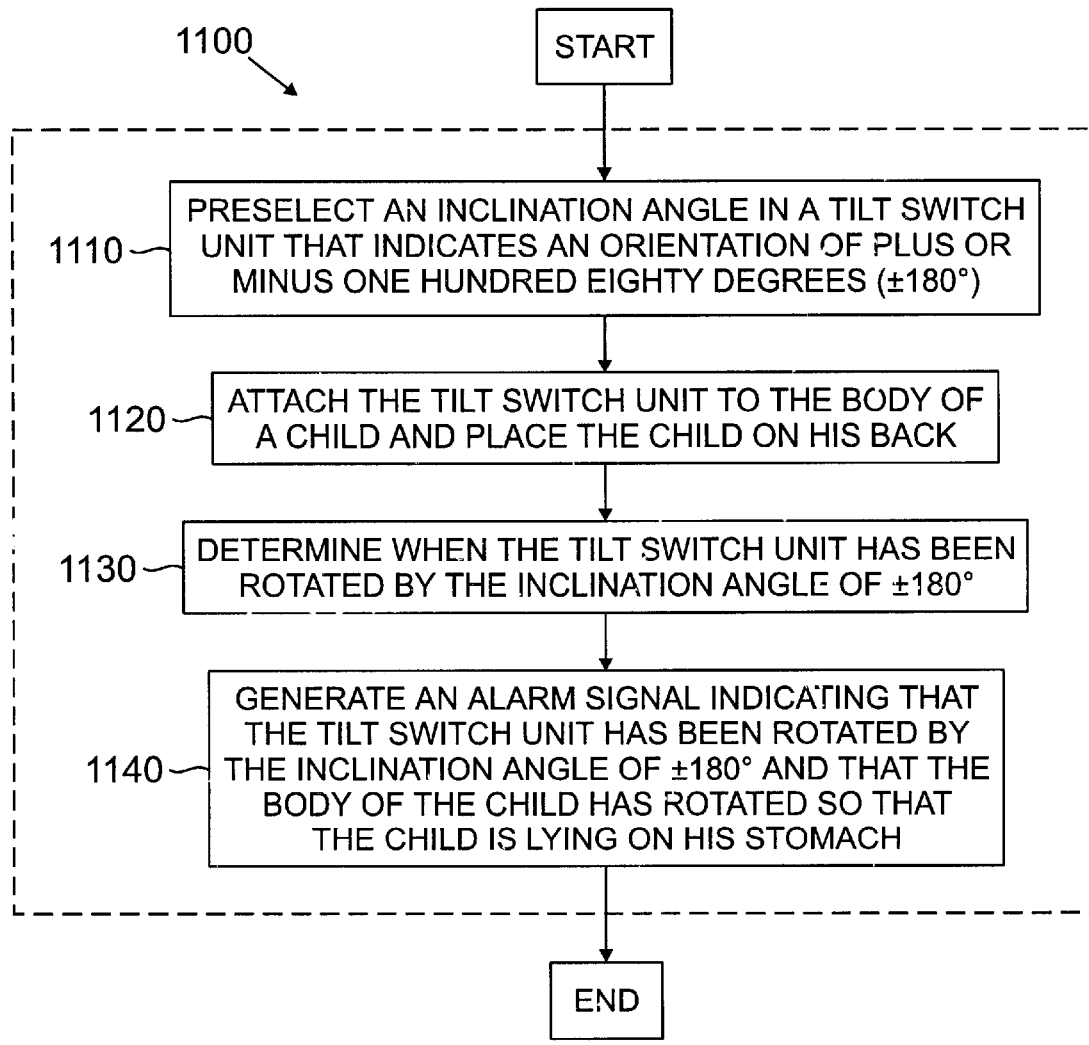
FIG. 11 is a flow diagram describing the logic of the operation of an advantageous embodiment of the present invention.

FIG. 11 is a flow diagram describing the logic of the operation of an advantageous embodiment of the present invention. The operation steps of the method of the present invention are collectively referred to in FIG. 11 as operation steps 1100. The first operation step 1110 comprises preselecting an inclination angle in tilt switch unit 300 that will indicate when a child 120 on his back has rolled over onto his stomach. The inclination angle is selected to be plus or minus one hundred eighty degrees (±180°).

The second operation step 1120 comprises attaching the tilt switch unit 300 to the body of child 120 and placing child 120 on his back. The third operation step 1130 comprises determining when the tilt switch unit 300 has been rotated by the inclination angle of plus or minus one hundred eighty degrees (±180°). The rotation of tilt switch unit 300 by the inclination angle of plus or minus one hundred eighty degrees (±180°) occurs when the child 120 on his back has rolled over onto his stomach.

The fourth operation step 1140 comprises generating an alarm signal that indicates that tilt switch unit 300 has been rotated by the inclination angle of plus or minus one hundred eighty degrees (±180°). The alarm signal indicates that the child 120 on his back has rolled over onto his stomach.

The invention is also capable of detecting a rotational movement of an inorganic body such as a shipping crate that contains a product that must be stored and shipped in an upright position. Products that must be kept in an upright position include, without limitation, jet engines, scientific equipment, and bearings for the rotating drums of washing machines and clothes dryers. The present invention can detect an undesired rotational movement of such an inorganic body during storage or shipping and immediately send an alarm signal. A supervisor can minimize potential damage to the body by immediately responding to the alarm signal and reversing the undesired rotational movement of the body.

Although the present invention has been described in detail, those skilled in the art should understand that they can make various changes, substitutions and alterations herein without departing from the spirit and scope of the invention in its broadest form.

What is claimed is:

1. An apparatus for detecting a rotational movement of a body of a child to which said apparatus is attached comprising:
    at least two tilt switches capable of determining when said apparatus has been rotated by a preselected inclination angle measured with respect to a vertical reference axis of rotation through the body of said child, and in response to said determination, generating an inclination signal; and a controller coupled to said at least two tilt switches capable of detecting said inclination signal from said at least two tilt switches, and in response to said detection, generating an alarm signal; and at least one physiological condition monitor capable of being coupled to said child for detecting signals that represent at least one physiological condition of said child, wherein said controller is coupled to said at least one physiological condition monitor, and wherein said controller, in response to detecting said inclination signal from said at least two tilt switches, is capable of initiating the operation of said at least one physiological condition monitor.

2. An apparatus as claimed in claim 1 wherein said preselected inclination angle is a clockwise rotation of approximately one hundred eighty degrees around said vertical reference axis of rotation, where said clockwise rotation indicates that the child has moved from a position of lying on the child's back to a position of lying on the child's stomach.

3. An apparatus as claimed in claim 1 wherein said preselected inclination angle is a counterclockwise rotation of approximately one hundred eighty degrees around said vertical reference axis of rotation, where said counterclockwise rotation indicates that the child has moved from a position of lying on the child's back to a position of lying on the child's stomach.

4. An apparatus as claimed in claim 1 wherein said controller receives said inclination signal for length of time that exceeds a preselected length of time before said controller generates said alarm signal.

5. An apparatus as claimed in claim 1 further comprising a signaling device coupled to said controller capable of receiving said alarm signal, and in response to receipt of said alarm signal, one of: (a) generating an audible alert and (b) wirelessly transmitting an alert message to a remote monitoring device and (c) transmitting an alert message to a remote monitoring device via a computer network.

6. A method for determining when a child has moved from a position of lying on its back to a position of lying on its stomach, comprising the steps of:

preselecting an inclination angle within at least two tilt switches, wherein said at least two tilt switches are capable of determining when said at least two tilt switches have been rotated by said preselected angle with respect to a vertical reference axis of rotation through the body of said child;

wherein a rotation by said preselected inclination angle indicates that said child has moved from a position of lying on its back to a position of lying on its stomach; and attaching said at least two tilt switches to said child;

determining when said at least two tilt switches have been rotated by said inclination angle; and initiating the operation of at least one physiological condition monitor attached to said child to monitor at least one physiological condition of said child in response to said determination that said at least two tilt switches have been rotated by said inclination angle.

7. The method as claimed in claim 6 wherein said inclination angle is a rotation of approximately one hundred eighty degrees around said vertical reference axis of rotation.

8. A method for alerting a care giver when one child of a plurality of children has moved from a position of lying on its back to a position of lying on its stomach, comprising the steps of:

attaching at least two tilt switches to each of said plurality of children;

preselecting an inclination angle within each of said at least two tilt switches attached to each of said plurality of children so that when one of each of said at least two tilt switches is rotated by said preselected inclination angle, then each one of said at least two tilt switches so rotated indicates that said child has moved from a position of lying on its back to a position of lying on its stomach;

determining when one of said at least two tilt switches attached to one child of said plurality of children has been rotated by said preselected inclination angle; and generating a signal in response to said determination to alert the care giver that said one child of said plurality of children has moved from a position of lying on its back to a position of lying on its stomach; and initiating the operation of at least one physiological condition monitor attached to said one child of a plurality of children to monitor at least one physiological condition of said one child of a plurality of children in response to said determination that said at least two tilt switches have been rotated by said inclination angle.

9. The method as claimed in claim 8 wherein said inclination angle is a rotation of approximately one hundred eighty degrees around said vertical axis of rotation.

* * * * *